United States Patent
Dahmen et al.

(10) Patent No.: US 8,870,758 B2
(45) Date of Patent: Oct. 28, 2014

(54) ENDOSCOPE WITH ADJUSTABLE VIEWING ANGLE

(75) Inventors: Jan Dahmen, Seitingen-Oberflacht (DE); Fang Lei, Durchhausen (DE)

(73) Assignee: Karl Storz GmbH & Co. KG (DE)

( * ) Notice: Subject to any disclaimer, the term of this patent is extended or adjusted under 35 U.S.C. 154(b) by 125 days.

(21) Appl. No.: 13/287,706

(22) Filed: Nov. 2, 2011

(65) Prior Publication Data

US 2012/0123212 A1 May 17, 2012

(30) Foreign Application Priority Data

Nov. 2, 2010 (DE) .......................... 10 2010 050 011

(51) Int. Cl.
*A61B 1/06* (2006.01)
*G02B 23/24* (2006.01)
*A61B 1/07* (2006.01)
*A61B 1/00* (2006.01)

(52) U.S. Cl.
CPC ........ *A61B 1/00167* (2013.01); *G02B 23/2423* (2013.01); *A61B 1/0008* (2013.01); *A61B 1/00183* (2013.01); *A61B 1/00098* (2013.01); *A61B 1/07* (2013.01)
USPC ............................ 600/173; 600/164; 600/178

(58) Field of Classification Search
USPC ................... 600/173–178, 182; 385/118, 119
See application file for complete search history.

(56) References Cited

U.S. PATENT DOCUMENTS

| | | | |
|---|---|---|---|
| 3,896,793 A * | 7/1975 | Mitsui et al. ................... | 600/104 |
| 4,841,949 A * | 6/1989 | Shimizu et al. ............... | 600/107 |
| 6,053,862 A | 4/2000 | Ono | |
| 6,923,757 B2 * | 8/2005 | Abe et al. ...................... | 600/130 |
| 2002/0107448 A1 | 8/2002 | Gandjbakhche et al. | |
| 2002/0188204 A1 | 12/2002 | McNamara et al. | |

FOREIGN PATENT DOCUMENTS

| | | |
|---|---|---|
| DE | 2428913 A1 | 1/1975 |
| DE | 10222686 A1 | 11/2002 |
| DE | 60015375 T2 | 2/2006 |
| EP | 2062545 A2 | 5/2009 |
| JP | 63155116 A | 6/1988 |

OTHER PUBLICATIONS

German Search Report; Application No. 10 2010 050 011.9; Issued: Jun. 20, 2011; 5 pages.
European Search Report; Application No. EP 11 18 6373; Issued: Feb. 9, 2012; Mailing Date: Feb. 22, 2012; 6 pages.

* cited by examiner

*Primary Examiner* — Alireza Nia
*Assistant Examiner* — Timothy J Neal
(74) *Attorney, Agent, or Firm* — St. Onge Steward Johnston & Reens LLC (57) ABSTRACT

An endoscope with adjustable viewing angle includes a light outlet device on the distal end of the endoscope to radiate illuminating light at an angle of illumination and a light conductor to transmit illuminating light to the light outlet device such that the light outlet device can be moved to adjust the angle of illumination in relation to the endoscope and such that a flexible portion of the light conductor is configured and positioned in order to be elastically reshaped when the light outlet surface is moved.

15 Claims, 4 Drawing Sheets

ENDOSCOPE WITH ADJUSTABLE VIEWING ANGLE

CROSS-REFERENCE TO RELATED APPLICATIONS

The present application claims priority of German patent application No. 10 2010 050 011.9 filed on Nov. 2, 2010.

FIELD OF THE INVENTION

The present invention relates to an endoscope with an adjustable viewing angle.

BACKGROUND OF THE INVENTION

In addition to endoscopes for medical and non-medical technical applications, whose viewing angle is parallel to the longitudinal axis of the endoscope shaft, endoscopes with other fixed viewing angles have been developed for some time. The viewing angle of an endoscope is understood here and hereinafter always to mean the direction facing from the distal end of the endoscope, in which an object is situated that appears in the center of the image recorded by means of the endoscope. In many applications, however, a fixed viewing angle is a disadvantage. In the worst case, for example during a medical procedure, the endoscope must be replaced numerous times. In such cases it is an advantage to use an endoscope with a viewing angle that can be selected or adjusted in situ.

Observing an object in a cavity by means of an endoscope assumes as a rule that there is some illumination of the object. For this purpose an endoscope comprises, for example, lightwave conductors, in particular glass fibers, by means of which an illuminating light is transmitted from the proximal end of the endoscope along the shaft to the distal end of the endoscope. Light outlet surfaces of the lightwave conductors on the distal end of the endoscope are positioned and configured in such a way that the entire visual field or viewing field is sufficiently illuminated.

In an endoscope with adjustable viewing angle, the illuminating light on the distal end of the endoscope, in the simplest case, is distributed in such a way that the entire visual field is illuminated independently of the particular viewing angle selected. This results, however, in a series of disadvantages. In particular, light capacity is wasted, because the entire visual fields of all selectable viewing angles are illuminated constantly, independently of the viewing angle that is actually selected. Thus, at a predetermined desired brightness, a markedly higher lighting capacity must be provided altogether than with an endoscope with a fixed viewing angle.

An additional disadvantage arises from the fact that illuminating light of high intensity can photothermally or photochemically damage tissue or other objects. With an endoscope with fixed viewing angle, the distal end of the endoscope is at too close a distance to an object, at least on observing the recorded image. In using a video camera on the endoscope, an automatic warning of users is also possible if the brightness of a recorded image exceeds a predetermined threshold. With an endoscope with adjustable viewing angle, however, part of the illuminating light impinges on objects lying outside the visual field. Therefore there is no undesired approach of the distal end of the endoscope to these objects, and no resulting illumination of these objects with too high a radiant capacity.

A further disadvantage consists in the fact that illuminating light radiated outside the visual field can also be dispersed or reflected by objects or opaque media. The reflected or dispersed illuminating light can arrive directly or indirectly in the observation beam path. Consequently, contrasts and the distinguishability of objects, especially in dark image areas, can be reduced.

An additional disadvantage comes from the fact that the illuminating intensity or intensity of the illuminating light is essentially constant in the direction in which the viewing angle can be varied (often referred to also as the vertical direction), while it decreases slightly as a rule toward the edge of the visual field in the direction perpendicular thereto (often also called the horizontal direction). However, users of endoscopes with fixed viewing angle are as a rule accustomed to an illuminating intensity that slightly declines toward the edge of the visual field both in the horizontal and in the vertical directions. The illuminating intensity that is constant in the vertical direction can therefore be experienced as an irritant.

Patent application DE 600 15 375 T2 describes an arrangement of several prisms. One of the prisms can be rotated around an axis in order to cast illuminating light at an adjustable viewing angle. The inventors of the present invention, however, have determined that in the described arrangement of prisms the distribution of the illuminating light inside the visual field is insufficient in many cases.

SUMMARY OF THE INVENTION

An object of the present invention consists in providing an improved endoscope with adjustable viewing angle.

This object is achieved through the contents of the independent claims.

Refinements are indicated in the dependent claims.

Embodiments of the present invention are based on the idea of reshaping the distal end of a light conductor depending on the angle of illumination or viewing angle in order to adjust the angle of illumination to an adjustable viewing angle of an endoscope. It thereby becomes possible to illuminate only the visual field in the momentarily selected viewing angle. This reduces the required total radiant capacity, the risk of photothermal or photochemical damage, and the intensity of dispersed light that reduces image contrast. In addition, with corresponding configuration of the light outlet device independently of the angle of illumination, it is possible to achieve a distribution of the illuminating light that is experienced as pleasant by users, in which the illuminating intensity in particular decreases on approaching all edges of the visual field.

An endoscope with adjustable viewing angle includes a light outlet device on the distal end of the endoscope for radiating illuminating light at an angle of illumination so that the light outlet device is moveable in relation to the endoscope in order to adjust the angle of illumination, and a light conductor to transmit illuminating light to the light outlet device so that a flexible portion of the light conductor is configured and positioned in order to be elastically reshaped when the light outlet device is moved.

The endoscope viewing angle, in particular, can be pivoted around a pivot axis that is perpendicular to the longitudinal axis of the shaft of the endoscope. The endoscope longitudinal axis is, in particular, the longitudinal axis of the shaft. In the case of a rigid, straight shaft, the longitudinal axis of the shaft is the straight line on which the center points of the cross-section surfaces of the shaft are situated. In the case of a flexible shaft, the endoscope longitudinal axis is the longitudinal axis of the distal end of the shaft, that is, the straight line on which the center points of the cross-section surfaces of the shaft are situated close to its distal end.

The light outlet device is configured in particular to be moved, especially pivoted, in synchronicity with the viewing angle of the endoscope. For this purpose, a guide device, for example, to guide the light outlet device, is mechanically coupled with a device to select the viewing angle in such a way that the angle of illumination essentially corresponds to the viewing angle at all times.

The light conductor includes in particular one or more light-conducting fibers, for example glass fibers or plastic fibers, to transmit illuminating light. The flexible portion of the light conductor, in particular, is situated on the distal end of the endoscope. For example, the flexible portion of the light conductor is immediately adjacent to the light outlet device or to a mounting for holding the distal end of the light conductor. The entire light conductor can be flexible. An elastic reshaping of the flexible portion is understood to mean a purely elastic or essentially elastic reshaping, so that the possibility of a partly structural reshaping is not excluded.

The light outlet device, in the simplest case, is a distal front surface of the light conductor that is configured as a light outlet surface. Alternatively, the light outlet device includes one or more lenses, mirrors, prisms or other optical elements for shaping a light bundle that is switched out of the light conductor on the distal end.

In particular, a high degree of effectiveness can be achieved with a configuration of the light outlet device as a light outlet surface on the distal end of the light conductor. It is possible to avoid losses by reflectances on the light inlet surfaces and light outlet surfaces of prisms as they are used in accordance with DE 600 15 375 T2.

An additional advantage consists in reduced manufacturing expense, in particular for adjustment, of the illuminating beam path to transmit illuminating light. For example, in using prisms in accordance with DE 600 15 375 T2, whereas each optical element must be precisely mounted and at the same time must be precisely aligned with respect both to translational and rotational degrees of freedom, primarily only the proximal end and the distal end of the light conductor must be adjusted with exactitude. Thus, in configuring the light outlet device as a light outlet surface on the distal end of the light conductor itself, a purely translational maladjustment has only a small impact on the quality of the illumination of an object observed by means of the endoscope. Precise adjustment of the distal light outlet surface of the light conductor merely with respect to rotational degrees of freedom can be advantageous or necessary.

An additional advantage in using a light conductor whose flexible portion is elastically reshaped in modifying the viewing angle, can consist in a comparatively small space requirement. In particular, the cross-section of the light conductor can be smaller than prisms which are used for example in DE 600 15 375 T2. When space is limited, the use of a flexible light conductor creates additional degrees of freedom for configuration.

In an endoscope as described here, the light conductor can include a bundle of light-conducting fibers, and a flexible mantle is foreseen in which the bundle of light-conducting fibers is positioned in the area of the flexible portion.

The flexible mantle is, for example, a shrink-tubing or other tube with circular or oval or other cross-section. The flexible mantle is made, for example, of rubber, silicon, an elastomer or other elastic synthetic material. The distal end of the flexible mantle, in particular, is directly contiguous with the light outlet device or a mounting for holding the distal end of the light conductor, or is permanently mechanically connected with the light outlet device or the mounting.

The flexible mantle can support the light conductor in its flexible portion, for example in order to facilitate a uniform reshaping of the light conductor and to avoid any buckling or increased curvature of the light conductor at particular points. The flexible mantle, in addition, can protect the light conductor from wear by rubbing on edges or surfaces and from other mechanical damage. Thus the flexible mantle can markedly reduce the risk of a defect to the flexible portion of the light conductor and markedly increase the service life of the flexible portion of the light conductor and thus of the entire endoscope.

An endoscope with a flexible mantle in the area of the flexible portion of the light conductor, as described here, can comprise a lubricant, which is placed in the mantle in order at least to reduce either friction inside the bundle of light-conducting fibers or friction between light-conducting fibers and the flexible mantle.

The lubricant, in particular, can be a powder (such as talcum), liquid, or a highly ductile substance and is secured by the flexible mantle on the flexible portion of the light conductor. In addition, materials that are known in the form of coatings can be used as gliding elements.

The use of a lubricant inside the mantle makes possible a marked reduction of friction or of friction forces (sliding friction and, in particular, static friction) between the light-conducting fibers as well as between the light-conducting fibers and the mantle. With reduced friction, the risk of breakage to individual light-conducting fibers markedly declines. This increases the life expectancy of the light conductor and of the entire endoscope. The use of the flexible mantle around the flexible portion of the light conductor makes it possible to employ lubricants, which otherwise would not be useable because of their consistency because they would flow or fall out of the bundle of light-conducting fibers.

In an endoscope as described here, in which the light conductor includes a bundle of light-conducting fibers, light-conducting fibers of the bundle can comprise a coating in order to reduce friction between the light-conducting fibers.

Regardless of whether the bundle in the area of the flexible portion is placed in a flexible mantle, the individual light-conducting fibers can comprise a coating to reduce friction. Aside from that, the advantages of a coating of the fibers to reduce friction resemble the aforementioned advantages of using a lubricant.

In an endoscope as described here, in which the light conductor includes a bundle of light-conducting fibers, the bundle can comprise a non-circular-shaped cross-section.

The bundle comprises in particular an essentially elliptical, oval or rectangular cross-section, so that the width or height of the cross-section in two directions perpendicular to one another is in a ratio of at least 3:2 or at least 2:1 or at least 5:1 or at least 10:1. In particular, the bundle comprises a cross-section whose height is less than its width, so that the height is measured in a direction in which the curvature of the light conductor is modified at its foreseen elastic reshaping, and where the width of the bundle is measured in a direction perpendicular thereto.

A non-circular cross-section of the bundle, in particular a flattened cross-section as described above, increases the flexibility of the bundle and reduces the mechanical impact of individual light-conducting fibers at the expected elastic reshaping of the light conductor. Consequently the risk of a defect in the light conductor can be reduced and the service life of the light conductor and of the entire endoscope can be increased.

In addition, owing to a non-circular cross-section of the bundle, the force required for the foreseen reshaping of the light conductor is reduced. As a result, devices for holding, guiding, and moving the light outlet device and for elastic reshaping of the light conductor can be of smaller dimension.

In addition, it is possible to reduce the forces required for adjusting the viewing angle and the angle of illumination as well as for elastically reshaping the light conductor.

An endoscope as described here can include a number of light conductors that each comprise a flexible portion, so that the flexible portion of each light conductor is configured and positioned so that it can be elastically reshaped when the light outlet device is moved.

With the same total cross-section and thus equal transmittable total radiant power, several light conductors each comprise a smaller cross-section than one individual light conductor. A number of light conductors can therefore have greater flexibility than one single light conductor. This can reduce the risk of a defect in a light conductor. In addition, when one light conductor fails, light can continue to be transmitted via other light conductors. Therefore a defect in one light conductor does not necessarily lead to a total failure of the endoscope.

The greater flexibility of a number of light conductors, each with a smaller cross-section, also has as a consequence that lesser forces are required to adjust the viewing angle and the angle of illumination and for the foreseen elastic reshaping of the light conductors.

The endoscope includes, in particular, two light conductors with flexible portions, so that each of the light outlet devices associated with the light conductors are positioned on two opposite sides of a light inlet window of an observation beam path. This arrangement of at least two light outlet devices can allow an illumination of the visual field that is especially low in shadow.

In an endoscope as described here, the light outlet device can pivot around a pivot axis.

Pivotability of the light outlet device around a pivot axis is especially advantageous when the viewing angle of the endoscope can be pivoted around a pivot axis. The pivot axis of the light outlet device in this case is, in particular, the pivot axis of the viewing angle. The pivot axis of the light outlet device is in particular perpendicular to the longitudinal axis of the endoscope or to the longitudinal axis of the endoscope shaft.

An endoscope as described here can, in addition, include a joint around which the light outlet device can be pivoted.

The joint includes, in particular, an axle, so that the axis of the axle is the pivot axis of the light outlet device. A configuration of the joint in this manner can make possible an easy and simultaneously precise guidance of the light outlet device.

In an endoscope with a joint that includes an axle, the axle can be configured in such a way that, when the light outlet device pivots, the light conductor can move past one end of the axle.

This configuration of the axle makes possible an especially large space inside which the light conductor can move during its reshaping. Thereby the required curvatures can be reduced or the required curvature gradients can be increased. As a result of a reduced curvature of the light conductor, the risk of a defect in the light conductor can be reduced, even with frequent reshaping, and the service life of the light conductor and endoscope can be increased. In addition, it becomes possible to reduce the forces required for adjustment of the viewing angle and angle of illumination as well as for the expected reshaping of the light conductor.

In an endoscope as described here, a sliding block guide can be provided to guide the light outlet device.

The sliding block guide is, in particular, arch-shaped or circularly arched. The sliding block guide, in particular, constitutes an alternative to a joint, but it can also be combined with an axle or another joint. The sliding block guide includes, in particular, a slide that is guided inside one or more guide grooves or on one or more studs or tracks.

An advantage of a sliding block guide can be found in the fact that no construction space is required for an axle or other joint. This leaves an especially large space available for the light conductor or conductors and for their movement.

An endoscope with a sliding block guide as described here can, in addition, comprise a force transmission device for transmitting a pushing or pulling force to the proximal end of the endoscope to move the light outlet device, and the force transmission device can be of a one-piece construction with a slide of the sliding block guide.

The force transmission device extends, in particular, from the distal end of the endoscope to the proximal end of the endoscope in order to transmit the pushing or pulling force from the proximal to the distal end of the endoscope. The force transmission device can be coupled on the proximal end of the endoscope with an operating device to move the light outlet device by means of the force transmission device.

The force transmission device includes, for example, a push rod, a pulling device, a coupling rod or other device, particularly rod-shaped or tubular-shaped. The force transmission device can be of bend-proof construction in such a way that it does not buckle under an expected maximum pushing or pressure. Alternatively or in addition, the force transmission device can be directed to one or more sites or in one or more sections in order to prevent buckling under impact from pushing or pressure.

A component that constitutes a force transmission device and the slide can be of thin, pliable construction, at least in the area of the sliding block guide, in order to enable adjustment to an arched shape of the guide grooves, studs and/or tracks. If the force transmission device, for example because of spring pressure on the distal end, is intended exclusively or predominantly to transmit drawing forces, the component that constitutes the force transmission device and slide can be of flexible configuration over its entire length. The same is true if the force transmission device is applied sufficiently to prevent buckling also in the case of a pushing or pressure impact. In this case the component that comprises the force transmission device and slide can be, for example, a thin, flexibly pliable metal plate.

If the force transmission device is expected to transmit more than a minor pushing or pulling force, the component that constitutes the force transmission device and slide can be of nonbuckling rigid construction or configuration in the area of the force transmission device in order to prevent buckling. In the event that the component that comprises the force transmission device and slide is configured as a pliable metal plate, resistance to bending is increased in the area of the force transmission device, for example through one or more longitudinal corrugations or through edges bent to form longitudinal flanges.

In an endoscope with a force transmission device as described here, the light conductor can be mechanically operated on the force transmission device.

In particular, the light conductor is mechanically rigidly connected with the force transmission device at least one site. Alternatively or in addition, the light conductor can be directed to the force transmission device in its longitudinal direction at one or more sites. Directing the light conductor in its longitudinal direction means that the light conductor can move in its longitudinal direction but not in both directions perpendicular to the longitudinal direction of the light conductor. The longitudinal direction of the light conductor corresponds in particular to the longitudinal direction of the force transmission device.

In an endoscope as described here, a center point of the light outlet device and a center point of the light inlet surface of the observation beam path are situated in particular in a plane parallel to a pivot axis of the viewing angle or in a plane perpendicular to the pivot axis of the viewing angle.

In the first case, the light outlet device is situated alongside the light inlet surface of the observation beam path in relation to the pivot direction of the angle of illumination and the viewing angle. In the second case, the light outlet device and light inlet surface of the observation beam bath are situated behind one another in relation to the pivot direction of the illuminating device and of the viewing angle. In both cases, to reduce the casting of shadows, two or more light outlet devices can be positioned in each case on at least two opposite sides of the light inlet surface of the observation beam path.

In an endoscope as described here, a device to adjust the viewing angle and the light outlet device can be mechanically coupled directly or indirectly on the distal end of the endoscope in order to allow a simultaneous movement of the viewing angle and of the angle of illumination.

The device to adjust the viewing angle includes, for example, a device to pivot a video camera and/or a light-sensitive sensor, prism, mirror or one or more other optical elements in the observation beam path of the endoscope. For direct coupling of the device to adjust the viewing angle and the light outlet device, they are positioned, for example, on a common axle or on a common sliding block guide. The common sliding block guide or common axle can be actuated or moved, for example, by means of the aforementioned force transmission device.

An indirect coupling can be required when one or more optical elements in the observation beam path and the light outlet device must be moved at different angles (for example, in a ratio of 1:2). An indirect coupling is possible, for example, on the proximal end on which an operating device to adjust the viewing angle is provided. Manual impact on the operating device can be transmitted to the distal end of the endoscope, for example via two separate axles, push rods, pulling elements, or coupling rods, first for pivoting the illuminating device by a movement of the light outlet device, and second to rotate the viewing angle.

If necessary, magnetic couplings, bellows pleats or insulations, mounted on the proximal and/or distal end, can be used for fluid-tight performance.

BRIEF DESCRIPTION OF THE DRAWINGS

Hereinafter, embodiments are described with reference to the appended drawings, which are as follows.

DETAILED DESCRIPTION OF THE INVENTION

Figure 1:
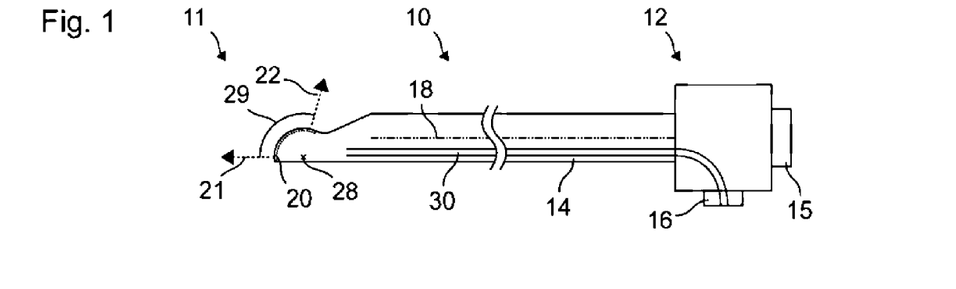
FIG. 1 shows a schematic depiction of an endoscope with adjustable viewing angle.

FIG. 1 shows a schematic depiction of an endoscope 10 with a distal end 11, a proximal end 12, and a rigid shaft 14 that extends from the distal end 11 to the proximal end 12. Alternatively, the shaft 14 is flexible or partly flexible. The cross-section of the shaft 14 or at least the outer contour of the cross-section of the shaft 14 is constant or essentially constant between the distal end 11 and the proximal end 12. In particular, the contour of the cross-section of the shaft 14 is circular or elliptical in shape. In this case the longitudinal axis 18 of the endoscope 10 illustrated in FIG. 1 is the axis of symmetry of the mantle surface of the shaft 14 between the distal end 11 and the proximal end 12. In a cylindrical mantle surface of the shaft 14, the longitudinal axis 18 is also the sum of the center points or surface centers of gravity of the cross-sections of the shaft 14 between the distal end 11 and the proximal end 12. In a cylindrical mantle surface of the shaft 14, the longitudinal axis 18 is also the axis of symmetry of the mantle surface.

On the distal end 11, the shape of the shaft 14 departs from the cylindrical symmetry as is depicted by way of example in FIG. 1. In particular, the shaft 14 comprises on the distal end 11 an opening that is closed by a transparent window component 20 with a vaulted surface. In particular, the window component 20 closes the opening with a hermetic sealing. The surface of the window component 20 has, for example, the shape of a portion of a cylindrical mantle, whereby the axis of symmetry of the cylinder is perpendicular to the longitudinal axis 18 of the endoscope 10 and to the plane of projection of FIG. 1. Alternatively, the surface of the transparent window component 20 has the shape of a portion of a spherical surface or of a rotation-symmetrical or non-rotation-symmetrical ellipsoid.

On the distal end 11 of the endoscope 10, optical devices are positioned in the shaft 14 that are not shown in FIG. 1. These optical devices make it possible to vary the viewing angle of the endoscope between a first extreme viewing angle 21 and a second extreme viewing angle 22. The viewing angle can pivot between the two extreme viewing angles 21, 22 around a pivot axis 28 that is perpendicular to the plane of projection of FIG. 1. The viewing angle in each case is the direction based on the distal end 11 of the endoscope 10 in which an object is situated that appears in the center of an image recorded by means of the endoscope 10.

In the example illustrated in FIG. 1, the first extreme viewing angle 21 is parallel or essentially parallel to the longitudinal axis 18 of the endoscope 10. Situated between the extreme viewing angles 21, 22 is an angle area 29 that comprises approximately 120 degrees in the illustrated example. Within this angle area, the viewing angle of the endoscope 10 can be displaced or adjusted, in particular, continually.

On the proximal end 12 the endoscope 10 comprises a first coupling 15 for optically coupling the endoscope 10 with a video camera or an eyepiece, as well as a second coupling 16 to couple the endoscope 10 with a light source via a light conductor cable. One or more light conductors 30 lead from the second coupling 16 through the shaft 14 to the distal end 11 of the endoscope 10. Illuminating light generated from a light source can be transmitted to the distal end 11 of the endoscope 10 via a light conductor cable, the second coupling 16, and the light conductor or conductors 30.

Figure 2:
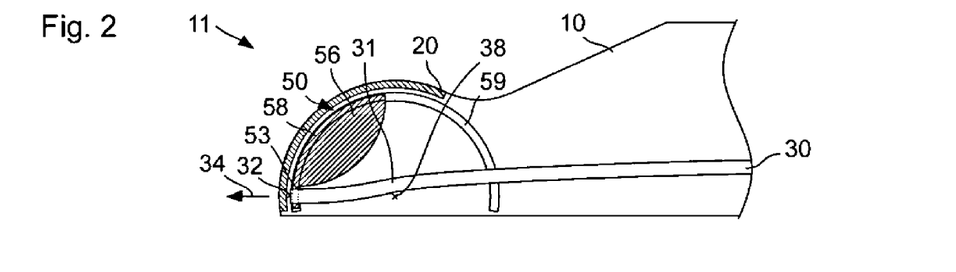
FIG. 2 shows a schematic depiction of an embodiment of the distal end of the endoscope from FIG. 1.
Figure 3:
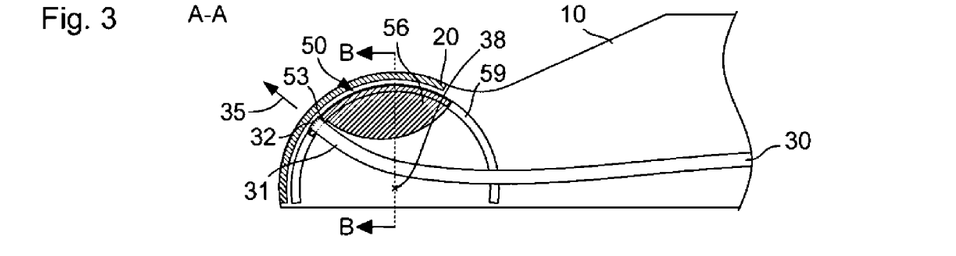
FIG. 3 shows another schematic depiction of the embodiment from FIG. 2.
Figure 4:
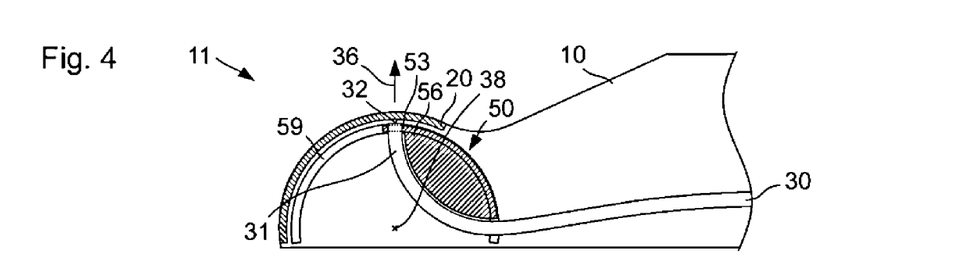
FIG. 4 shows another schematic depiction of the embodiment from FIGS. 2 and 3.
Figure 5:
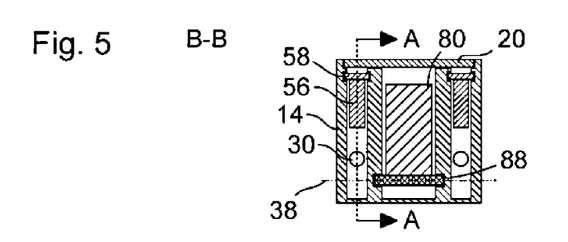
FIG. 5 shows another schematic depiction of the embodiment from FIGS. 2 through 4.

FIGS. 2 through 5 show schematic depictions of an embodiment of the distal end 11 of the endoscope 10 presented above with reference to FIG. 1. FIGS. 2 through 4 show mutually corresponding depictions of sections along a plane A-A parallel to the plane of projection of FIG. 1. The position of the sectional plane A-A is indicated in FIG. 5. FIG. 5 shows a schematic depiction of a section along a sectional plane B-B perpendicular to the planes of projection or sectional planes of FIGS. 1 through 4. Some of the parts of the endoscope that are described below are positioned differently in the depictions in FIGS. 2 through 4. Only FIGS. 3 and 5 correspond to one another with respect to the arrangement of these elements. The approximately quadrilateral outer contour of the cross-section shown in FIG. 5 constitutes a simplification; in fact the cross-section can depart from it, for example with an at least partly circular-shaped outer contour.

On the distal end 11 of the endoscope 10, the lightwave conductor 30 comprises a flexible portion 31 and a light outlet surface 32. The light conductor 30 includes, for example, a bundle of light-conducting fibers whose ends are cut off and polished in a plane in order to form the light outlet surface 32. The light outlet surface 32 constitutes a simple form of a light outlet device. In addition, a light outlet device, contrary to the depiction in FIGS. 2 through 4, can comprise one or more lenses, prisms, mirrors or other optical elements for forming beams.

On its distal end 11 the endoscope 10 comprises a guide device 50 to guide the light outlet surface 32 of the light conductor 30. The guide device 50 includes a slide 58 with a mounting 53 for the light conductor 30. The mounting 53 includes, for example, a pass-through borehole in which the light conductor 30 is joined close to the light outlet surface 32, for example by means of cement.

The slide 58 in the example shown in FIGS. 2 through 5 has essentially the shape of a bent plate that forms part of a cylindrical mantle. Two edges of the slide 58, which are opposite one another and of circular shape, are fed in guide grooves 59 in the shaft 14 of the endoscope or in the housing that forms the shaft 14. The guide groove 59 is of circular shape. In addition, the guide device 50 comprises a mounting device 56.

FIGS. 2 through 4 show the slide 58 as well as the mounting device 56 and light outlet surface 32 of the light conductor 30, which are rigidly connected with the slide 58, in three different positions. The slide 58, the light outlet surface 32 and the mounting device 56 can be moved between the positions shown in FIGS. 2 through 4. Guiding the slide 58 in the circular-shaped grooves 59 here forces the slide 58, the light outlet surface 32 and mounting device 56 on circular tracks around a pivot axis 38. Geometric center points of the circular-shaped guide grooves 59 are situated on the pivot axis 38. In the positions of the light outlet surface 32 shown in FIGS. 2 through 4, illuminating light transmitted by the light conductor 30 is, depending on the case, uncoupled or radiated in the first angle of illumination 34 (FIG. 2), in the second angle of illumination 35 (FIG. 3) or in the third angle of illumination 36 (FIG. 4).

In displacing or moving the light outlet surface 32 with the slide 58 and the mounting device 56 between the positions shown in FIGS. 2 through 4, the elastic portion 31 of the light conductor 30 is elastically reshaped. In the first angle of illumination 34, shown in FIG. 2, the light conductor 30 runs essentially straight. In the second angle of illumination 35, shown in FIG. 3, the elastic portion 31 of the light conductor is slightly bent. In the third angle of illumination 36, shown in FIG. 4, the elastic portion 31 of the light conductor 30 is even more strongly bent than in the second angle of illumination 35, shown in FIG. 3.

A circular-shaped mounting surface of the mounting device 56 causes a uniform curvature of the elastic portion 31 of the light conductor 30, in particular in the third angle of illumination 36, and prevents buckling or irregular curvature of the elastic portion 31 of the light conductor 30.

It can be recognized particularly in FIG. 5 that there is a great deal of space available for the light conductor 30. Even at extreme viewing angles 21, 22 (compare FIG. 1), this allows a comparatively weak curvature of the elastic portion 31 of the light conductor 30 and thus reduces the risk of a defect.

Also recognizable in FIG. 5 is a video camera 80, which is fastened so that it can rotate on an axle 88 around the pivot axis 38 of the angle of illumination. Owing to the pivotable nature of the video camera 80, the endoscope 10 comprises a pivotable viewing angle, as was described above with reference to FIG. 1. Contrary to the depiction in FIG. 5 in which the pivot axis 38 of the angle of illumination, described above with reference to FIG. 1, corresponds to the pivot axis 28 of the viewing angle, the video camera 80 can be pivoted around a pivot axis parallel to the pivot axis 38 of the angle of illumination The pivot axis 28 of the viewing angle 21, 22 and the pivot axis 38 of the angle of illumination 34, 35, 36 therefore are not required to be identical. Parallelism of the two pivot axes 28, 38 is, however, advantageous in many cases. Instead of a video camera 80, one or more prisms, mirrors or other optical elements can also be provided to adjust the viewing angle.

Figure 6:
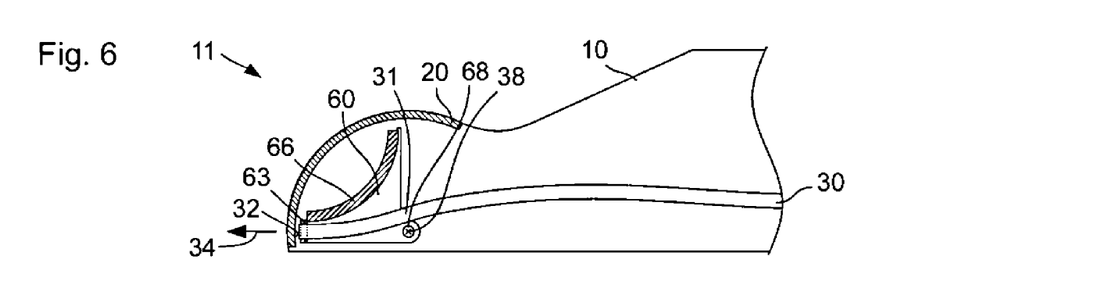
FIG. 6 shows a schematic depiction of an additional embodiment of the distal end of the endoscope from FIG. 1.
Figure 7:
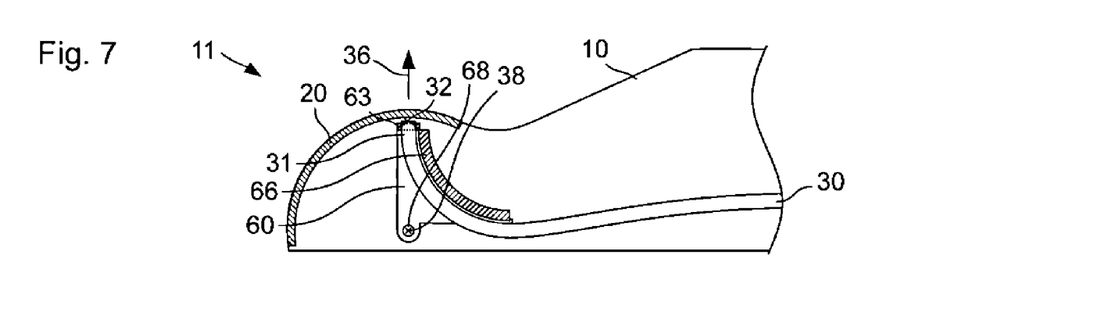
FIG. 7 shows another schematic depiction of the embodiment from FIG. 6.
Figure 8:
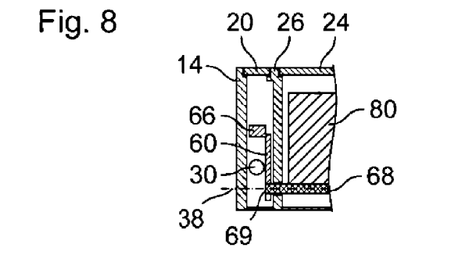
FIG. 8 shows another schematic depiction of the embodiment from FIGS. 6 and 7.

FIGS. 6 through 8 show schematic depictions of an additional embodiment of the distal end 11 of the endoscope 10 that is described above with reference to FIG. 1. FIGS. 6 and 7 show schematic depictions of a section along a plane parallel to the plane of projection of FIG. 1 and corresponding to the planes of projection of FIGS. 2 through 4. FIG. 8 shows a schematic depiction of a section along a plane perpendicular to the planes of projection or sectional planes of FIGS. 1, 6 and 7. Because the depiction in FIG. 8 does not correspond to either FIG. 6 or FIG. 7 in terms of the position of the devices to be described hereinafter, the sectional planes or their positions are not named or indicated in FIGS. 6 through 8.

The embodiment of FIGS. 6 through 8 resembles in some respects the embodiment presented above with reference to FIGS. 2 through 5. The embodiment in FIGS. 6 through 8 is distinguished from the embodiment presented above with respect to FIGS. 2 through 5, in particular, in that no slides and no guide groove are provided to guide the light outlet surface 32 of the light conductor 30. Instead, a guide device 60 with a mounting 63 is provided to hold the light conductor 30 close to its light outlet surface 32. The guide device 60 comprises a mounting device 66, which resembles in its form and function the mounting device in the embodiment of FIGS. 2 through 5. Contrary to the embodiment of FIGS. 2 through 5, the guide device 60 is secured on an axle 68 and can pivot with it around the pivot axis 38 of the angle of illumination.

In FIGS. 6 and 7, the guide device 60 and light outlet surface 32 are shown in the first angle of illumination 34 (see FIG. 2) or in the third angle of illumination 36 (see FIG. 4).

The angle of illumination and the light outlet surface 32 can freely rotate with the guide device 60 around the pivot axis 38 between the positions shown in FIGS. 6 and 7 in order to select any desired angles of illumination, at least between the first angle of illumination 34 and the third angle of illumination 36.

In particular in the cross-section shown in FIG. 8, it can be recognized that a large space is available to the light conductor 30 in pivoting the light outlet surface 32 around the pivot axis 38. The space available to the light conductor 30 is not restricted by the axle 68, especially because of the position of the end 69 of the angle 68. Therefore the light conductor 30 in the first angle of illumination 34 can run even more clearly straight, contrary to the depiction in FIG. 6. In the third angle of illumination 69 in particular, the mounting device 66 ensures a uniform curvature of the elastic portion 31 of the light conductor 30.

It can further be seen in FIG. 8 that a video camera 80 is positioned on the axle 68 of the guide device. Thus, by means of a rotation of the axle 68, the light outlet surface 32 of the light conductor 30, the angle of illumination and the video camera 80 and thus also the viewing angle are pivoted simultaneously. The axle 68 thus directly couples the guide device 60 and/or the light outlet surface 32 that is rigidly connected with the guide device 60 on the one hand, and the video camera 80 on the other hand. Thus the axle 68 also couples their movements.

In the embodiment of FIGS. 2 through 5, a continuous or common window component 20 is provided, through which it is possible both for illuminating light to emerge from the distal end 11 of the endoscope 10 and for light emanating from an observed object to enter the distal end 11 of the endoscope 10. This is particularly recognizable in FIG. 5. The space in which illuminating light can expand is separated or optically isolated by a wall from the space in which the video camera 80 is positioned only up to the inner surface of the window component 20.

Several separate window components are foreseen in the embodiment of FIGS. 6 through 8. A window component labeled with reference number 20 is foreseen for the emergence of illuminating light from the distal end 11 of the endoscope 10. An additional window component 24 is provided to admit light emanating from an observed object into the distal end 11 of the endoscope 10. The two window components 20, 24 are separated by a dividing wall 26 or its peripheral area, which is not translucent. The dividing wall 26 is configured in particular to separate the area in which illuminating light expands from the area in which the video camera is positioned up to the outer surface of the endoscope 10, completely and especially imperviously to light. This prevents any switching of illuminating light that is dispersed in the window component 24 or on its surface into the video camera 80.

A continuous window component or several separate window components can be foreseen in each of the embodiments described here—that is, both in the embodiments of FIGS. 2 through 5 and 6 through 8 and in embodiments described subsequently with reference to FIGS. 10 through 15. In addition, a continuous window component, as can be recognized in FIG. 5, can be provided with a light-absorbent separating layer that prevents an undesired direct switching of illuminating light into the video camera 80. Such a separating layer can be generated by ions that are implanted or introduced locally in other ways into the material of the window component.

Figure 9:
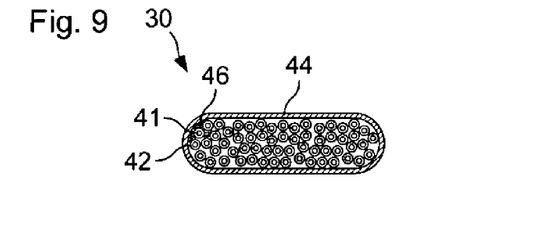
FIG. 9 shows a schematic depiction of a cross-section of a light conductor.

Shown in particular in FIGS. 5 and 8 are circular cross-sections of the light conductor 30. FIG. 9 shows an alternative cross-section of the light conductor 30, which can be employed in both of the embodiments described above with reference to FIGS. 2 through 8. The light conductor includes a flat bundle of light-conducting fibers 41, which each comprise a coating 42 to reduce friction. The bundle of light-conducting fibers 41 is mounted in a flexible mantle 44. Said flexible mantle 44 surrounds the bundle of light-conducting fibers 41 of the light conductor 30 in particular in its elastic portion 31 and extends to the mounting 53, 63 of the guide device 50, 60 (compare FIGS. 2 through 4, 6, 7).

Talcum or another pulverized, liquid, or highly ductile lubricant 46 can be placed inside the mantle 44 between the light-conducting fibers 41 to reduce friction between the light-conducting fibers 41 as well as between the light-conducting fibers 41 and the mantle 44. The mantle 44 prevents the lubricant 46 from falling or flowing out of the bundle of light-conducting fibers 41 and can thus contribute to its long-term effectiveness.

Contrary to the depiction in FIG. 9, the light conductor 30 can comprise either only coatings 42 on the light-conducting fibers 41 or only a lubricant 46 between uncoated light-conducting fibers 41.

FIG. 9 shows an oval cross-section whose border comprises two circular-arched and two straight portions. Contrary to the depiction in FIG. 9, the light conductor can comprise a cross-section that is of elliptical, circular or any other shape.

Figure 10:
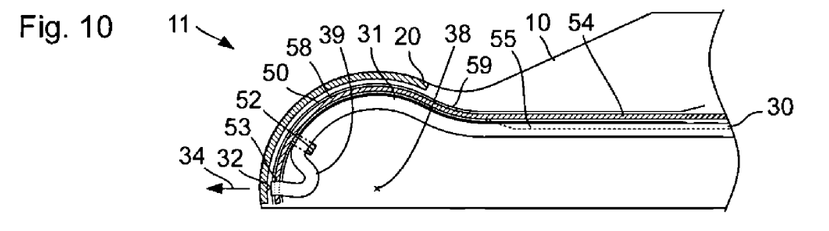
FIG. 10 shows a schematic depiction of another embodiment of the distal end of the endoscope from FIG. 1.
Figure 11:
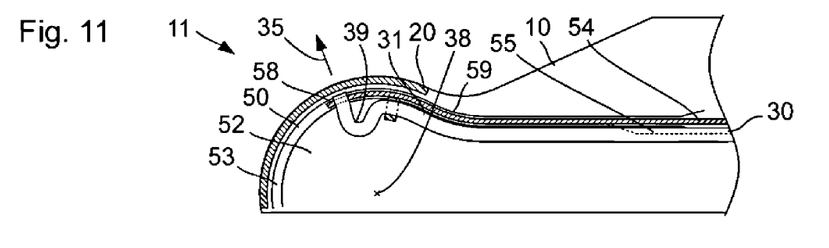
FIG. 11 shows another schematic depiction of the embodiment from FIG. 10.

FIGS. 10 and 11 show schematic depictions of an additional embodiment of the distal end 11 of the endoscope 10 presented above with reference to FIG. 1 in sections along a plane parallel to the plane of projection of FIG. 1 and corresponding to the planes of projection of FIGS. 2 through 4, 6 and 7. The distal end 11 of the endoscope 10 is shown in FIGS. 10 and 11 at two different angles of illumination 34, 35.

The embodiment of FIGS. 10 and 11 resembles the embodiments described above with reference to FIGS. 2 through 8 in some characteristics. In particular, the embodiment of FIGS. 10 and 11 includes a slide that resembles the slide presented above with reference to FIGS. 2 through 5. Contrary to the embodiment of FIGS. 2 through 5, the slide 58 is built as a single unit combined with a force transmission device 54. Said force transmission device 54 extends from the proximal end 12 to the distal end 11 of the endoscope 10. At the proximal end 12 of the endoscope 10, the force transmission device 54 is mechanically and/or magnetically coupled with an operating device, in particular, by means of which the force transmission device can be slid along the shaft 14 of the endoscope 10 to adjust the angle of illumination 34, 35.

The slide 58 and force transmission device 54 are, in particular, made up of a pliable metal plate that extends from the proximal end 12 to the distal end 11 of the endoscope 10. Two parallel borders of the metal plate are fed on and near the distal end 11 of the endoscope 10 in two guide grooves 59 opposite one another, only one of which is shown in FIGS. 10 and 11. A distal portion of the guide groove 59 runs essentially in an arched line parallel to the curved window component 20. The center point of the arc described by the guide groove is situated on the pivot axis 38 of the illuminating device 34, 35.

The metal plate that forms the slide 58 and force transmission device 54 comprises a longitudinal ribbing 55 in the area in which the metal plate forms the force transmission device 54. The longitudinal ribbing 55 stiffens the basically pliable metal plate to the point where the force transmission device maintains a straight shape and does not buckle even when a predetermined pressure or pushing force is applied. The proximal ends of the guide grooves 59 are positioned in such a way, and the longitudinal ribbing 55 extends so far in the distal direction, that the guide groove 59 and longitudinal ribbing 55 overlap or at least are only at a small distance apart and so that the longitudinal ribbing 55 is situated on a straight portion of the guide groove 59 at every viewing angle 34, 35. This ensures that, on the one hand, the portion of the metal plate forming the force transmission device 54 can undergo a pressure or pushing force at any time without buckling and that, on the other hand, the portion of the metal plate forming the slide 58 can be reshaped and moved back and forth with little resistance in the curved portion of the guide groove 59.

If the guide groove 59 extends as far as the proximal end 12 of the endoscope 10, the metal plate forming the slide 58 and force transmission device 54 can also resist buckling from pressure or pushing force even without a longitudinal ribbing 55. The longitudinal ribbing 55, moreover, can be dispensed with if the force transmission device 54 must undergo only pulling forces or only inconsequential pressure or pushing forces. For this purpose, the distal end 11 of the endoscope 10, for example, can include a spring or other elastic component that constantly draws the slide 58 and with it the force transmission device 54 in the direction toward the position that corresponds to the angle of illumination 34 shown in FIG. 10.

The distal end of the light conductor 30 is held rigidly on the slide 58 by a mounting 53 close to the light outlet surface 32 of the light conductor 30. In addition, the light conductor is held on the slide 58 by a clamp 52 or similarly working device close to its distal end. The light conductor 30 comprises a strongly curved portion 39 between the clamp 52 and the mounting 53. The light conductor 30 is of rigid construction in the strongly curved portion 39 and does not reshape itself when the viewing angle 34, 35 changes. If the light conductor 30 comprises a bundle of lightwave conductors, they are cemented or merged, for example, in the strongly curved portion 39. Instead of the illustrated curvature, the light conductor in the portion 39 can be curved in a different manner. A weaker curvature can be achieved by using more space. Instead of the strongly curved portion 39, one or more prisms, for example, can be foreseen.

Proximally from the clamp 52, the light conductor 30 is mounted in a flexible hose, for example, which is fastened to the metal plate that forms the slide 58 and force transmission device 54. As a result of the flexible hose, the light conductor 30 is directed in its longitudinal direction; that is, the light conductor 30 can move in its longitudinal direction, but not in directions that are at angles to it. As a result of this arrangement, a defined reshaping of the light conductor 30 can be achieved with maximum curvature radii or minimal curvature. Instead of the longitudinal ribbing 55, the light conductor that is conducted on the force transmission device 54 can be produced of non-pliable material in the corresponding portion, for example by cementing or merging of individual lightwave conductors that form the light conductor 30. Alternatively, the force transmission device 54 can be of tubular configuration in the corresponding portion, so that the light conductor is directed in the tubular force transmission device 54.

Figure 12:
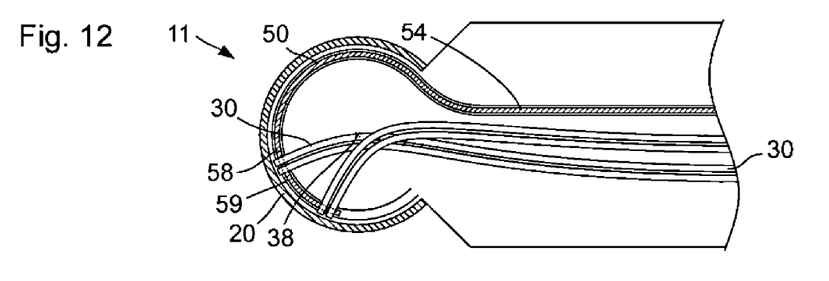
FIG. 12 shows a schematic depiction of an additional embodiment of the distal end of the endoscope from FIG. 1.
Figure 13:
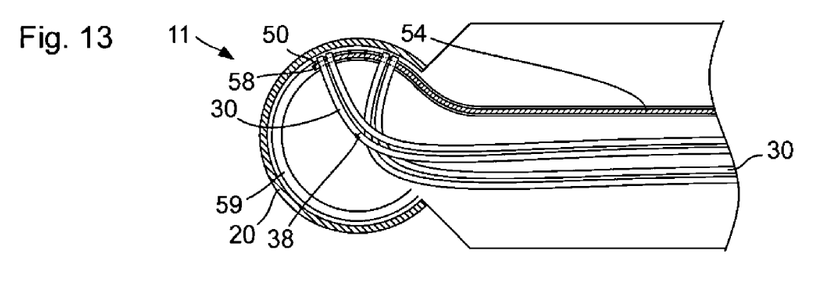
FIG. 13 shows another schematic depiction of the embodiment from FIG. 12.

FIGS. 12 and 13 show schematic depictions of an additional embodiment of the distal end 11 of the endoscope 10 described above with reference to FIG. 1 in sections along a plane parallel to the plane of projection of FIG. 1 and corresponding to the planes of projection of FIGS. 2 through 4, 6, 7, 10 and 11. The distal end 11 of the endoscope 10 is illustrated in FIGS. 12 and 13 at two different angles of illumination.

The embodiment of FIGS. 12 and 13 resembles the embodiment presented above with reference to FIGS. 10 and 11 in a few respects. In particular, the embodiment of FIGS. 12 and 13 includes a slide 58, which is produced as a single unit with a force transmission device 54. Contrary to the embodiment of FIGS. 10 and 11, in the embodiment of FIGS. 12 and 13 the guide grooves 59 extend along the entire shaft 14 of the endoscope. This option was already described above with reference to FIGS. 10 and 11. Because of the complete feeding of the force transmission device 54 in continuous guide grooves, the force transmission device 54, even without longitudinal ribbing, can absorb pressure or pushing forces without buckling.

An additional difference from the embodiment of FIGS. 10 and 11 consists in the fact that in the embodiment of FIGS. 12 and 13, instead of one light conductor there are several light conductors foreseen, whose light outlet surfaces for example are positioned on opposite sides of a light inlet surface of an observation beam path. Each individual light conductor 30 comprises a smaller cross-section than the light conductor in the embodiment of FIGS. 10 and 11. Each individual light conductor 30 therefore comprises higher elasticity or can be reshaped by a lesser force. In addition, lesser mechanical tensions and less friction occur inside the individual light conductors 30.

In comparison with FIGS. 12 and 13, it can be seen that the required curvature radii of the light conductors 30 are large or the required curvatures are small. In particular, the required curvature radius even in a large pivot area can be greater than the radius of the shaft. This reduces the risk of breakage or other damages in the areas of the light conductor 30 that are reshaped in modifying the angle of illumination.

In the depiction of the embodiments of FIGS. 2 through 8, no additional details were given on devices for displacing or adjusting the viewing angle, in particular the guide devices 50, 60. A force transmission device similar to the force transmission devices presented above with reference to FIGS. 10 through 13 can be foreseen, in particular, also in the embodiment of FIGS. 2 through 5. Here the force transmission device, in particular close to the distal end of the slide 58 or close to the mounting 53 of the light conductor 30, is connected with the slide 58 in order to permit a large angle area in moving the viewing angle 34, 35.

Figure 14:
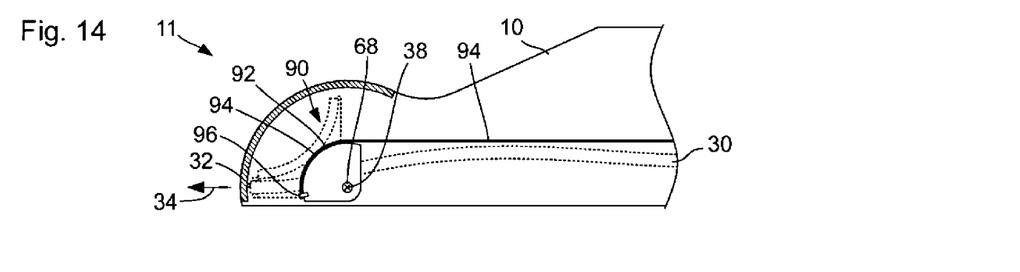
FIG. 14 shows a schematic depiction of an additional embodiment of the distal end of the endoscope from FIG. 1.
Figure 15:
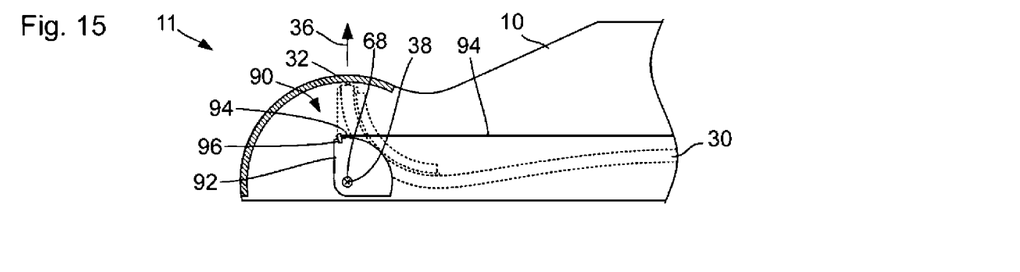
FIG. 15 shows another schematic depiction of the embodiment from FIG. 14.

FIGS. 14 and 15 show schematic depictions of a device 90 to transmit a force to a movable light outlet surface 32 or other light outlet device on the distal end 11 of an endoscope 10 and to move the light outlet device to adjust the angle of illumination 34, 36. The planes of projection of FIGS. 14 and 15 are parallel to the planes of projection of FIGS. 2 through 4, 6, 7 and 10 through 13. The distal end 11 of the endoscope 10 is depicted in FIGS. 14 and 15 at two different angles of illumination 34, 36. By way of example, devices and characteristics of the embodiment of FIGS. 6 through 8 are shown in broken lines. A description of the devices and characteristics shown in broken lines in FIGS. 14 and 15 can be found in the presentation of the embodiment of FIGS. 6 through 8.

The device 90 includes a disc device 92 that is fastened to an axle 68. The disc device 92 can rotate with the axle 68 around a pivot axis 38. The light outlet surface 32 that is indicated only in broken lines in FIGS. 14 and 15 is, in particular, mechanically coupled with the axle 68. A pivoting motion of the disc device 92 therefore results in a corresponding pivoting motion of the light outlet surface and illuminating device 34, 36. The disc device 92 comprises a rounded edge portion whose curvature center point is situated on the pivot axis 38.

A belt device 94 extends in the shaft of the endoscope 10 from the proximal end 12 of the endoscope 10 to the distal end 11 of the endoscope 10. The belt device 94 includes, in particular, a wire or a band of metal or plastic and has low stretch elasticity. The distal end of the belt device is mechanically connected with the disc device 92 by means of a fastening device 96.

It can be recognized from a comparison of FIGS. 14 and 15 that a movement of the belt device 94 in the longitudinal direction of the shaft of the endoscope 10 causes a pivoting motion of the disc device 92, light outlet surface 32 and angle of illumination 34, 36. In a pivoting motion of the disc device 92 in clockwise direction, a distal area of the belt device 94 is lifted from the arched border portion of the disc device 92. In a pivoting motion of the disc device 92 in counterclockwise direction, a distal area of the belt device 94 is placed or coiled onto the arched border portion.

The belt device 94, in particular, is rigid only under pulling tension and cannot transmit pushing forces. In order nevertheless to make possible a pivoting motion of the disc device 92, light outlet surface 32 and angle of illumination 34, 36 in counterclockwise direction, a spring or other elastic element, in particular, is provided on the distal end 11 of the endoscope 10, but is not shown in FIGS. 14 and 15. Said spring or other elastic element pre-tenses the disc device 92 and the light outlet surface 32 in the direction toward the position shown in FIG. 14.

What is claimed is:

1. An endoscope with adjustable viewing angle, comprising:
    a light outlet device on the distal end of the endoscope for radiating illuminating light at an angle of illumination so that the light outlet device can be moved to adjust the angle of illumination in relation to the endoscope;
    a light conductor for transmitting illuminating light to the light outlet device, such that a flexible portion of the light conductor is configured and positioned in such a way as to be elastically reshaped when the light outlet device is moved,
    a sliding block guide mechanically coupled to the light outlet device for guiding the movement of the light outlet device, the sliding block guide including a guide groove of arch-shape or circularly arch shape and a slide being guided inside the guide groove so that the slide and the light outlet device are movable on circular tracks around a pivot axis; and
    a force transmission device to transmit a pushing or pulling force to the proximal end of the endoscope to move the light outlet device,
    wherein the force transmission device is configured as a single unit with the slide of he sliding block guide.

2. The endoscope according to claim 1, wherein the light conductor includes a bundle of light-conducting fibers, in addition with:
    a flexible mantle in which the bundle of light-conducting fibers is positioned in the area of the flexible portion.

3. The endoscope according to claim 2, in addition with a lubricant that is positioned in the mantle in order at least to reduce either friction inside the bundle of light-conducting fibers or friction between light-conducting fibers and the flexible mantle.

4. The endoscope according to claim 1, wherein the light conductor includes a bundle of light-conducting fibers such that light-conducting fibers of the bundle comprise a coating to reduce friction between the light-conducting fibers.

5. The endoscope according to claim 1, wherein the light conductor includes a bundle of light-conducting fibers such that the bundle comprises a non-circular cross-section.

6. The endoscope according to claim 1, wherein the endoscope includes a number of light conductors, such that the flexible portion of each light conductor is configured and positioned in such a way as to be elastically reshaped when the light outlet device is moved.

7. The endoscope according to claim 1, in addition with a joint around which the light outlet device can pivot.

8. The endoscope according to claim 7, wherein the joint includes an axle such that the axle is configured in such a way that the light conductor can be moved past one end of the axle when the light outlet device pivots.

9. The endoscope according to claim 1, wherein the light conductor is mechanically directed on the force transmission device.

10. The endoscope according to claim 1, wherein the light outlet device further comprises one or more one lenses, prisms, mirrors, other optical forming beams, or video cameras.

11. The endoscope according to claim 1, wherein the pivot axis is perpendicular to a longitudinal axis of a shaft of the endoscope.

12. The endoscope according to claim 1, wherein the sliding block guide further includes a mounting device of a circular-shaped mounting surface.

13. The endoscope according to Claim 1, wherein the slide and the force transmission device are made up of a pliable metal plate.

14. The endoscope according to claim 13, wherein the metal plate includes a longitudinal ribbing in the area in which the metal plate forms the force transmission device.

15. The endoscope according to claim 1, wherein the force transmission device comprises a disc device fastened to an axle, wherein the disc device is rotatable with the axle around a pivot axis, and wherein the disc device having a rounded edge portion whose curvature center point is situated on the pivot axis.

* * * * *